United States Patent
Sherburne

[11] Patent Number: 5,292,250
[45] Date of Patent: Mar. 8, 1994

[54] VISUAL INDICATING DENTAL HANDPIECE SHEATH

[76] Inventor: Eugene G. Sherburne, 8905 Orleans Dr., Baton Rouge, La. 70810

[21] Appl. No.: 11,982
[22] Filed: Feb. 1, 1993
[51] Int. Cl.[5] .............................................. A61C 1/16
[52] U.S. Cl. ...................................................... 433/116
[58] Field of Search ......................................... 433/116

[56] References Cited

U.S. PATENT DOCUMENTS

| | | | |
|---|---|---|---|
| 684,951 | 10/1901 | Rothkranz | 433/116 |
| 1,162,941 | 12/1915 | Martin et al. | 433/116 |
| 1,539,253 | 5/1925 | Fuller | 433/116 |
| 1,742,061 | 12/1929 | Curry | 433/116 |
| 4,266,935 | 5/1981 | Hoppe | 433/116 |
| 4,693,871 | 9/1987 | Geller | 433/116 |
| 4,728,290 | 3/1988 | Eisner et al. | 433/116 |
| 4,752,223 | 6/1988 | Carlson | 433/116 |
| 4,789,336 | 12/1988 | Lewis | 433/116 |

*Primary Examiner*—John J. Wilson

[57] ABSTRACT

A visual indicating dental handpiece sheath designed to provide protection from the transmission of microbial diseases in dentist's surgical theatres. The sheath, comprised of a gasket and a three layer laminate of plastic film and paper is attached to the high-speed dental handpiece by an elastic band. The gasket and film act to control the intake of fluids and particulate matter, which may contain infectious diseases such as Hepatitis or AIDS, by the dental handpiece. The paper layer contains a water-soluble dye which is activated through use of the handpiece, and which indicates the unhygienic condition of a used sheath.

1 Claim, 2 Drawing Sheets

VISUAL INDICATING DENTAL HANDPIECE SHEATH

BACKGROUND OF THE INVENTION

1. Field of the Invention

This invention relates generally to dentistry and, more particularly, to methods and apparatus to remove the high-speed dental handpiece as a source of the transmisssion of disease.

Significant concern exists that the dentist's surgical theatre is a source of the transmission of microbial disease such as Hepatitis and Acquired Immune Deficiency Syndrome, among others.

The high-speed dental handpiece is a commonly used instrument, known to collect saliva, blood, grit and other particulate matter, and which may be a source of virus transmission.

Thus it is necessary to provide a barrier to exclude this matter from the handpiece, and to effectively stop any spread of such disease. This apparatus should be designed to be discarded after each use of the handpiece. This apparatus should also be readily determined to be in an unused condition by visual inspection, so that no error would result in a contaminated handpiece being used in the mouth of the next patient.

2. Description of the Prior Art

There have been various devices that have been proposed for the exclusion of matter from the handpiece:

| Name | U.S. Pat. No. |
| --- | --- |
| Carlson | 4,752,223 |
| Eisner et al. | 4,728,290 |
| Geller | 4,693,871 |
| Hoppe | 4,266,935 |
| Fuller | 1,539,253 |
| Martin/McTavish | 1,162,941 | but these have not proven to be satisfactory as they include no method for the visual determination of the hygiene of the handpiece. That is to say that no means is available to determine if the apparatus has been used or not.

SUMMARY OF THE INVENTION

The invention is comprised of: a form-fitting covering/sheath for use on the high-speed dental handpiece. The sheath is composed a gasket, a laminate of three layers of various materials and an elastic band to retain the sheath onto the handpiece. The gasket is made of felt treated with germicide. The gasket and laminate contain apertures which allow the rotable mounting of the dental burr, and the protrusion of the air/water jet and light.

The laminate is composed of:

an inner layer of plastic film, a middle layer of paper which has been treated with a water-soluble, non-toxic dye, and an outer layer of absorbent white paper.

In operation, the apparatus is mounted onto the handpiece with the elastic band. The felt gasket serves to provide a physical and germicidal barrier to the intake of contaminants by the handpiece, while allowing the dental burr, water/air jets and lights to protrude.

The plastic film layer of the laminate acts to restrict the movement of contaminants toward the gasket.

The middle paper layer of the laminate is treated with a water-soluble dye which is activated during use of the handpiece.

The outer paper layer of the laminate absorbs the dye exuded by the middle layer providing a visual indication of the unhygienic status of the sheath.

The elastic band is fixed to the laminate, and attaches the apparatus to the handpiece.

OBJECTS AND ADVANTAGES OF THE INVENTION

It is an object of the invention to provide a physical barrier to the intake of fluids or particulate matter into the dental handpiece.

It is another object of the invention to provide a germicidal barrier to the intake of microbial agents, contained in fluids or particulate matter, into the dental handpiece.

It is another object of the invention to provide a visual indication of the hygienic or unhygienic status of the handpiece.

It is another object of the invention to provide apparatus of this character that is simple in construction and operation.

It is a further object of the invention to provide apparatus of this character that is relatively inexpensive to manufacture and maintain.

The characteristics and advantages of the invention are further sufficiently referred to in connection with the following detailed description of the accompanying drawings, which represent one embodiment.

After considering this example, skilled persons will understand that many variations may be made without departing from the principles disclosed and I contemplate the employment of any structure, arrangements or modes of operation that are properly within the scope of the appended claims.

BRIEF DESCRIPTION OF THE DRAWINGS

Referring to the drawings which are for illustrative purposes only.

DESCRIPTION OF THE PREFERRED EMBODIMENT

Figure 1:
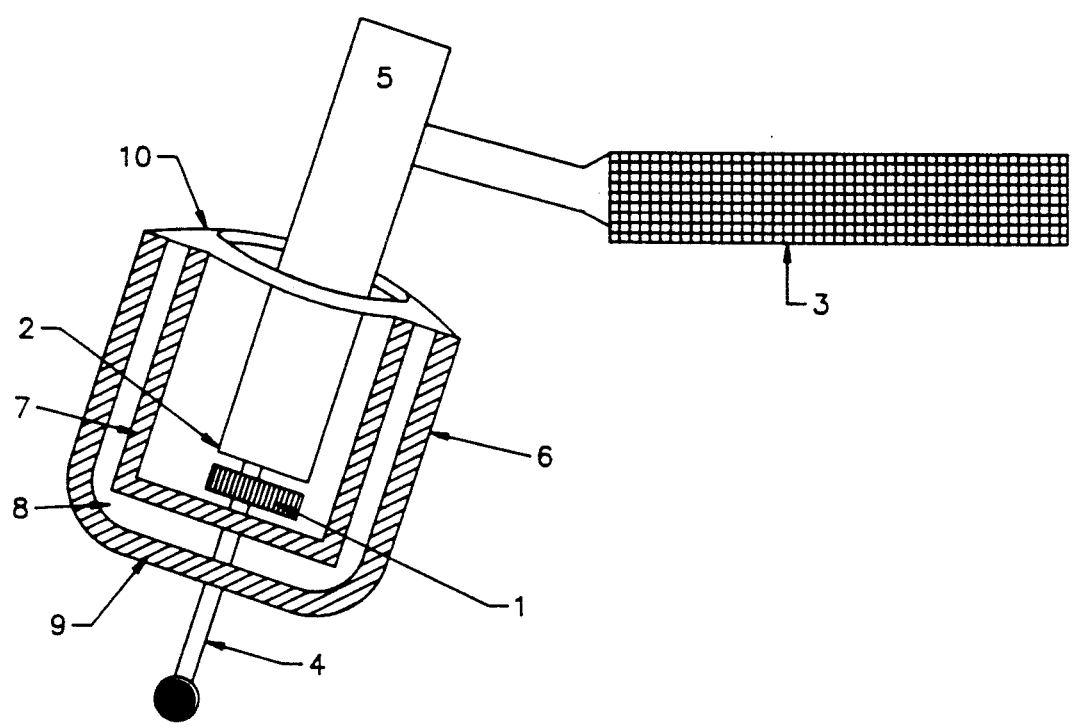
FIG. 1 is a schematic side view of apparatus embodying the present invention showing the gasket, laminate layers, and elastic band.

Referring to the drawings, in FIG. 1, there is shown apparatus embodying the present invention. A gasket (1), in this case felt, although other materials may be used if desired, is positioned at the face (2) of the handpiece (3). The dental burr (4) protrudes through the gasket. The gasket is impregnated with germicide so as to provide both a physical and a germicidal barrier to the intrusion of fluids or particulate matter containing infectious matter into the handpiece head (5). The laminate (6) contains three layers: the inner plastic film layer (7) which serves as a physical barrier to contaminants; a middle layer (8) composed of paper containing a water-soluble dye which is activated by the use of the handpiece in the mouth of a patient; and an outer paper layer (9) which absorbs the dye exuded by the middle layer, and which indicates the unhygienic status of the apparatus. The laminate (6) is shown surrounding the head (5).

The elastic band (10) is fixed to the laminate (6) and attaches the apparatus to the head (5). The elastic band (10) is sized so as to snugly surround and firmly grip the head (5). It is positioned the distance back from the face (2) of the handpiece (3) which pulls the laminate (6) and the gasket (1) tightly against the face (2). The laminate and gasket do not rotate with the burr (4).

Figure 2:
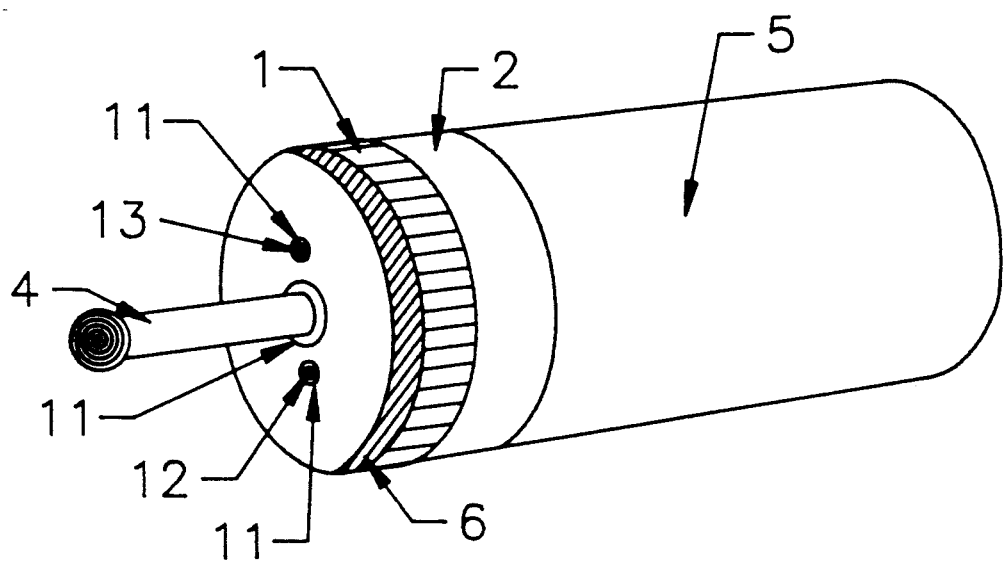
FIG. 2 is a schematic cross-section of apparatus embodying the present invention, showing detail of the gasket, laminate and orificies, at the face of the handpiece.

In FIG. 2 the gasket (1) is shown at the face (2) of the head (5). Orifices (11) are shown in the gasket and the laminate (6) which allow the rotable mounting of the dental burr (4) and the protrusion of the air/water jet (12) and light (13). The gasket (1) and the laminate (6), however, are held rigidly in place on the face (2) of the handpiece (3) by the grip of the elastic band (10) and do not rotate.

The invention and its attendant advantages will be understood from the foregoing description and it will be apparent that various changes may be made in the form, construction and arrangement of the parts without departing from the spirit or scope thereof or sacrificing its material advantages, the arrangement hereinbefore being merely by way of example; and I do not wish to be restricted to the specific form shown or uses mentioned except as defined in the accompanying claims.

I claim:

1. A visual indicating dental handpiece sheath designed for use on a dental handpiece and which provides a physical and germicidal barrier to the intake of contaminated fluids and particulate matter into the high-speed dental handpiece, to eliminate the transfer of contagious diseases among a dentist's patients comprising:
   a germicide impregnated gasket which is for positioning on the face of the handpiece so that it acts as a physical and germicidal barrier to fluids and particulate matter containing infectious agents,
   a laminate positioned above the gasket which consists of three layers comprised of:
   an inner layer of plastic film which acts as a physical barrier to fluids and particulate matter,
   a middle layer of water-soluble dye impregnated paper, which dye is activated by fluids generated during patient treatment,
   an outer layer of absorbent paper which absorbs the dye exuded from the middle layer and which provides a visual indication of an unhygienic sheath and handpiece,
   said gasket and laminate having orifices in them to allow for the rotable mounting of the dental burr, and the protrusion of air/water jets and light,
   and an elastic band fixed to the laminate, which is used to attach the sheath to the handpiece.

* * * * *